(12) United States Patent
Rugolo et al.

(10) Patent No.: US 10,720,141 B1
(45) Date of Patent: Jul. 21, 2020

(54) TYMPANIC MEMBRANE MEASUREMENT

(71) Applicant: X Development LLC, Mountain View, CA (US)

(72) Inventors: Jason Rugolo, Mountain View, CA (US); Cyrus Behroozi, Menlo Park, CA (US); Benoit Schillings, Los Altos Hills, CA (US)

(73) Assignee: X Development LLC, Mountain View, CA (US)

( * ) Notice: Subject to any disclaimer, the term of this patent is extended or adjusted under 35 U.S.C. 154(b) by 0 days.

(21) Appl. No.: 16/234,999

(22) Filed: Dec. 28, 2018

(51) Int. Cl.
*G10K 11/16* (2006.01)
*G10K 11/178* (2006.01)
(Continued)

(52) U.S. Cl.
CPC ............ *G10K 11/178* (2013.01); *A61B 1/227* (2013.01); *A61B 5/05* (2013.01); *A61B 5/126* (2013.01);
(Continued)

(58) Field of Classification Search
CPC .... G10K 11/16; G10K 11/172; G10K 11/175; G10K 11/178; H04R 1/10; H04R 1/1008; H04R 1/1016; H04R 1/1025; H04R 1/105; A61B 1/227; A61B 1/233; A61B 5/12; A61B 5/121; A61B 5/123; A61B 5/125; A61B 5/126; A61B 5/05; A61B 5/0515; A61B 5/0522; A61B 5/053; A51F 11/08; A51F 11/10; A51F 11/12; G06F 3/16; G06F 3/162; G06F 3/165; G06F 3/167; G06F 16/60; G06F 16/61; G06F 16/632; G06F 16/634; G06F 16/635; G06F 16/636;
(Continued)

(56) References Cited

U.S. PATENT DOCUMENTS 4,654,871 A 3/1987 Chaplin et al.
2004/0234094 A1 11/2004 Saunders et al.
(Continued)

FOREIGN PATENT DOCUMENTS

KR 101399222 B1 * 5/2014

OTHER PUBLICATIONS

U.S. Appl. No. 16/235,360, Transparent Sound Device, filed Dec. 28, 2018, 29 pages.
(Continued)

*Primary Examiner* — Leshui Zhang
(74) *Attorney, Agent, or Firm* — Christensen O'Connor Johnson Kindness PLLC

(57) ABSTRACT

An in-ear device includes a housing shaped to hold the in-ear device in an ear, and an audio package, disposed in the housing, to emit sound. A tympanic membrane measurement unit (TMMU) is structured to measure a movement of a tympanic membrane in the ear caused by external sound received by the tympanic membrane, and a controller is coupled to the audio package and the TMMU. The controller includes logic that when executed by the controller causes the in-ear device to perform operations. The operations include measuring a movement of the tympanic membrane, and in response to measuring the movement of the tympanic membrane, outputting sound from the audio package to destructively interfere with the external sound received by the tympanic membrane.

20 Claims, 6 Drawing Sheets

(51) Int. Cl.
*H04R 1/10* (2006.01)
*A61F 11/08* (2006.01)
*A61B 1/227* (2006.01)
*A61B 5/05* (2006.01)
*A61B 5/00* (2006.01)
*A61B 5/12* (2006.01)
*A61F 11/14* (2006.01)

(52) U.S. Cl.
CPC ............ *A61B 5/4836* (2013.01); *A61F 11/08* (2013.01); *H04R 1/1016* (2013.01); *A61F 2011/145* (2013.01)

(58) Field of Classification Search
CPC .... G06F 16/637; G06F 16/638; G06F 16/639; G06F 16/64
USPC ..... 381/318, 320, 83, 92, 93, 313, 108, 107, 381/97, 98, 100, 101, 102, 328, 60, 56, 381/57, 58, 321, 94.1–94.9, 72, 73.1, 74, 381/28, 59, 55, 317, 26, 71.1–71.14, 332, 381/96, 99, 103, 106, 120, 121; 700/94; 379/406.01–406.16; 455/569.1, 570; 704/E19.014, E21.002, E21.004, E21.007
See application file for complete search history.

(56) References Cited

U.S. PATENT DOCUMENTS

| | | |
|---|---|---|
| 2009/0080670 A1 | 3/2009 | Solbeck et al. |
| 2009/0097681 A1* | 4/2009 | Puria .................... H04R 25/405 381/318 |
| 2009/0299215 A1 | 12/2009 | Zhang |
| 2013/0018216 A1* | 1/2013 | Beckerle ............ A61N 1/36036 600/25 |
| 2018/0014113 A1* | 1/2018 | Boesen ................ H04R 1/1091 |
| 2018/0113673 A1* | 4/2018 | Sheynblat ............... G10L 17/00 |

OTHER PUBLICATIONS

U.S. Appl. No. 16/235,417, Open-Canal In-Ear Device, filed Dec. 28, 2018, 23 pages.
U.S. Appl. No. 16/235,092, Optical Otoscope Device, filed Dec. 28, 2018, 27 pages.
U.S. Appl. No. 16/176,660, Modular In-Ear Device, filed Oct. 31, 2018, 30 pages.

* cited by examiner

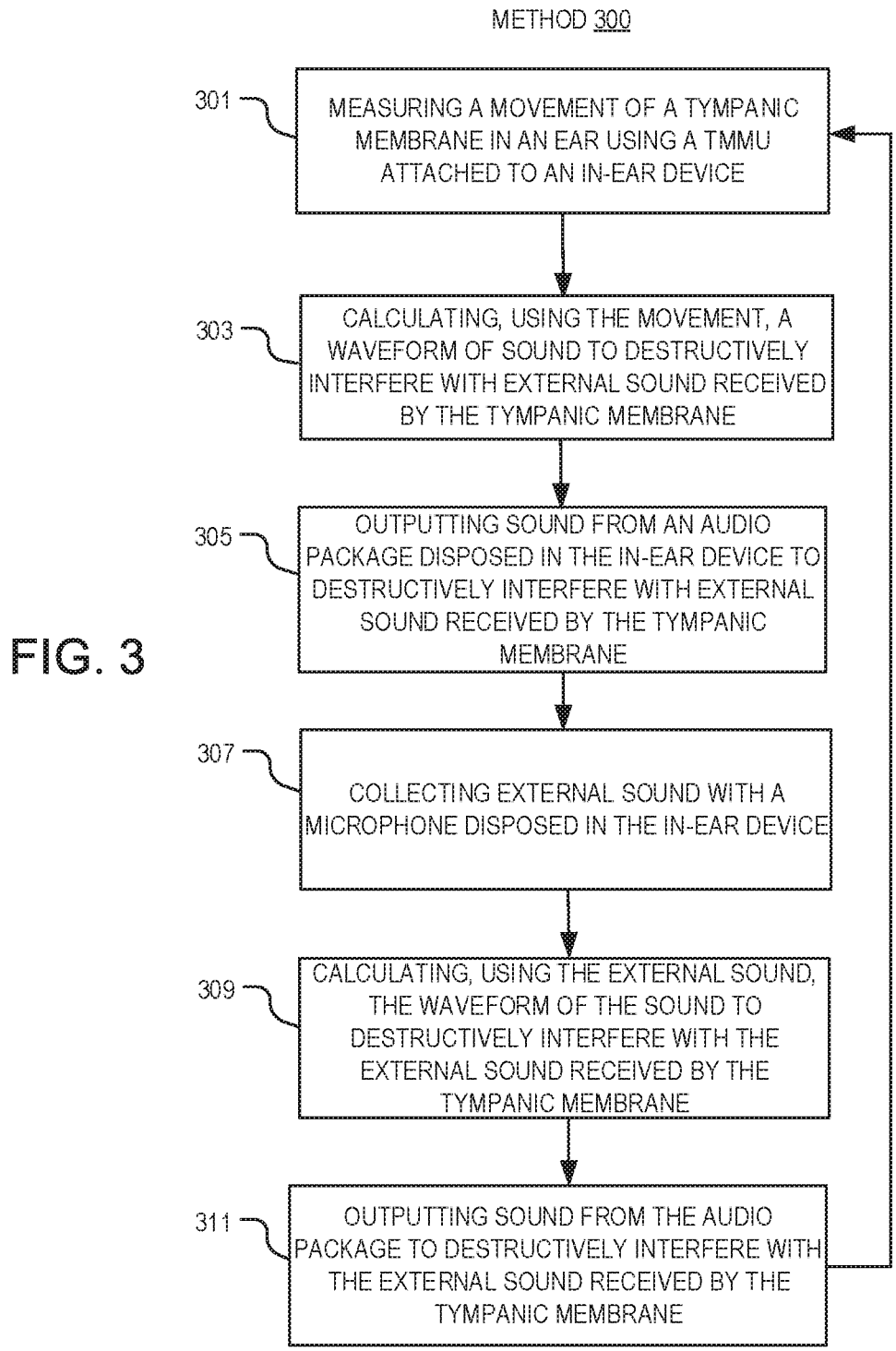

US 10,720,141 B1

TYMPANIC MEMBRANE MEASUREMENT

TECHNICAL FIELD

This disclosure relates generally to in-ear devices.

BACKGROUND INFORMATION

Headphones are a pair of loudspeakers worn on or around a user's ears. Circumaural headphones use a band on the top of the user's head to hold the speakers in place over or in the user's ears. Another type of headphones are known as earbuds or earpieces and consist of individual monolithic units that plug into the user's ear canal.

Both headphones and ear buds are becoming more common with increased use of personal electronic devices. For example, people use head phones to connect to their phones to play music, listen to podcasts, etc. However, even the best noise canceling devices suffer from imperfect cancellation that can leave users disoriented or still hearing certain undesirable sounds.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. Not all instances of an element are necessarily labeled so as not to clutter the drawings where appropriate. The drawings are not necessarily to scale, emphasis instead being placed upon illustrating the principles being described.

FIG. 3 illustrates a method of using an in-ear device, in accordance with an embodiment of the disclosure.

DETAILED DESCRIPTION

Embodiments of a system, apparatus, and method for a tympanic membrane measurement are described herein. In the following description, numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Generally, ear-worn monitors are useful for displaying sounds to the human ear while on the go. Music, directions, digital assistants, and ambient sound modification are all things people desire. Often times, high quality sound augmentation can only be achieved when you can properly eliminate natural sounds. For example, to "delete" the loud train noise from your perceived audio field, you must be able to occlude it or actively cancel it. However, sound cancellation technologies are imperfect at best. Passive occlusion may not provide enough blockage to fully remove sound, and these devices may be uncomfortable to wear for extended periods of time, (e.g., professional music, construction, etc.). Other noise canceling devices that use active sound cancellation may do so imprecisely due to the complexity of incoming sounds and the individual user's head transfer function.

Accordingly, embodiments in accordance with the teachings of the present disclosure herein actively measure the tympanic membrane (a membrane forming part of the hearing organ, which vibrates in response to sound waves and allows people and animals to hear sound), and, using the tympanic membrane measurement, produce sound waves that destructively interfere with external sounds (e.g., sounds originating outside of the ear). Thus, a more complete and accurate form of active noise cancellation can be achieved.

The following disclosure will describe the embodiments discussed above, and other embodiments, as they relate to the figures.

Figure 1:
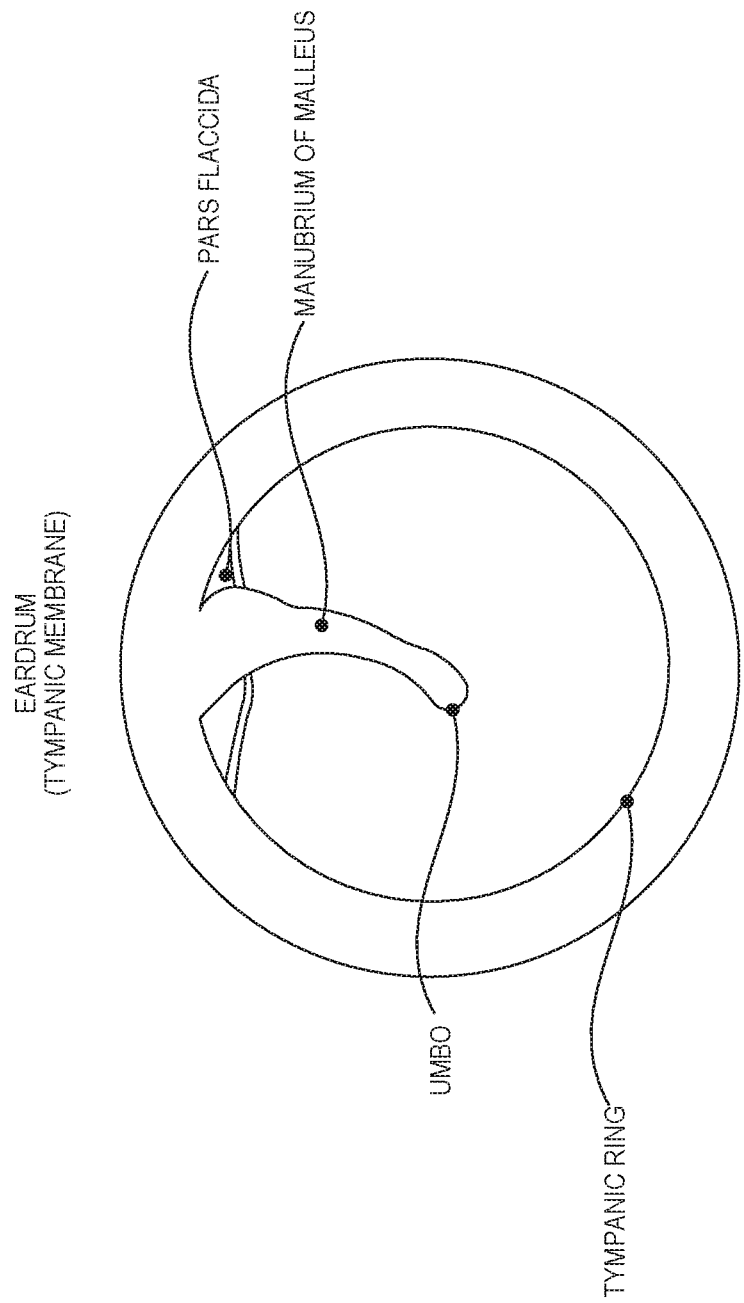
FIG. 1 is a cartoon illustration of a human tympanic membrane.

FIG. 1 is a cartoon illustration of a human tympanic membrane (or ear drum). Depicted are the locations of the pars flaccida (the triangular, flaccid portion of the tympanic membrane that attaches directly to the petrous bone), manubrium of malleus (attached to the medial surface of the membrane, drawing it toward the tympanic cavity), umbo (the most depressed aspect of the concave surface of the manubrium), and tympanic ring (part of the temporal bone forming an incomplete circle for the attachment of the circumference of the tympanic membrane). As will be described in examples below, different measurement techniques may be used to measure the movement of the tympanic membrane. The various techniques may measure the deflection at any of the parts depicted, and other parts, in accordance with the teachings of the present disclosure.

Figure 2A:
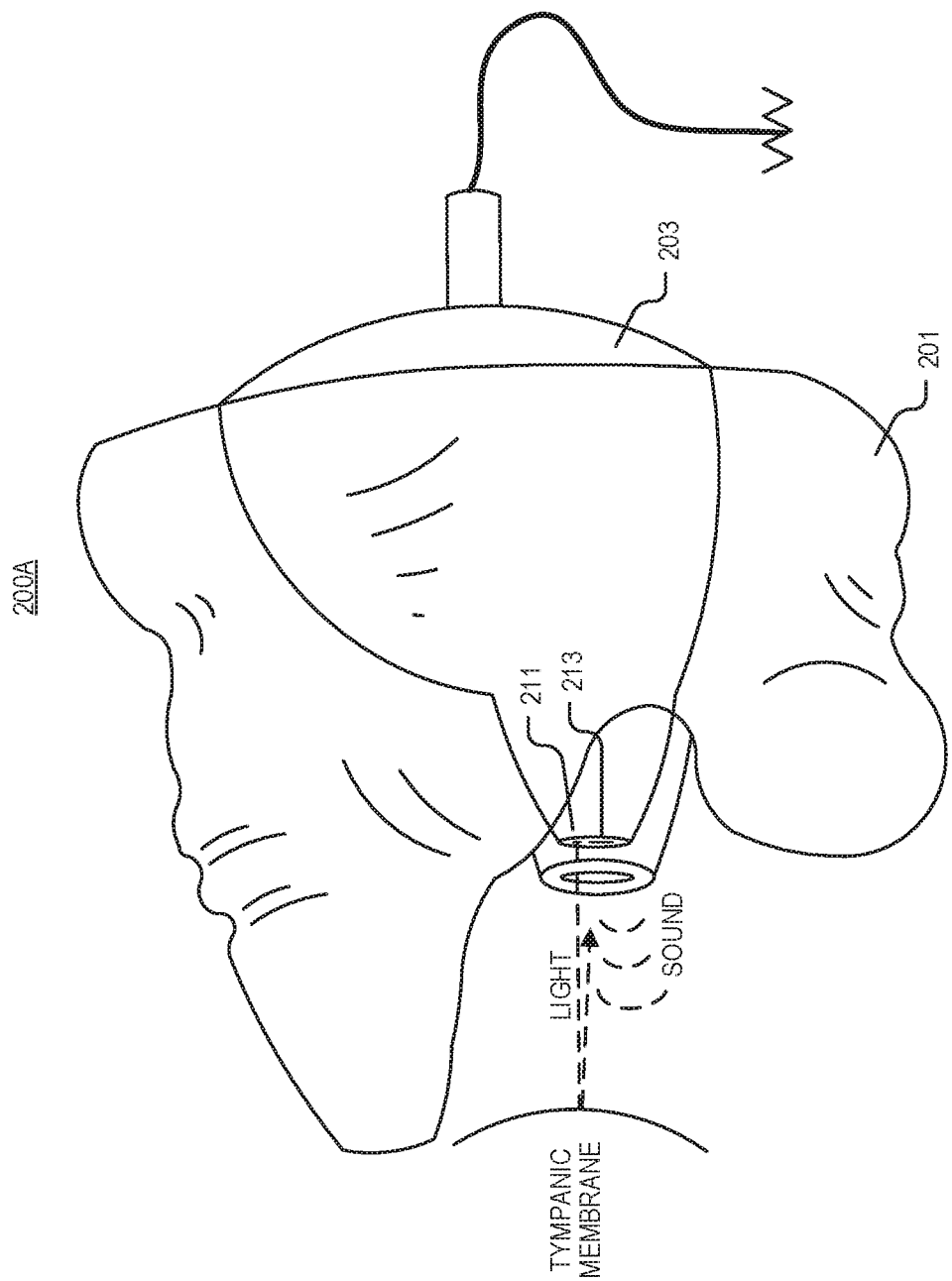
FIG. 2A illustrates an in-ear device, in accordance with an embodiment of the disclosure.

FIG. 2A illustrates an in-ear device 200A, in accordance with an embodiment of the disclosure. Depicted are housing—including both molding 201 (e.g., a soft polymer, like silicone that may be custom designed to fit in the user's ear for long term use), and casing 203 (e.g., a hard plastic casing to hold electronic devices and friction fit inside a hollowed out portion of molding 201)—one or more optical emitters 211 (e.g., light emitting diodes or lasers which may emit, ultraviolet, visible or infrared light) and one or more optical receivers 213 (e.g., a one or two dimensional array of photodiodes to detect deflection of a light beam from emitters 211). It is appreciated that there may be one in-ear device 200A for each ear (e.g., two in-ear devices 200 may be provided as a set).

In the illustrated embodiment, the housing is shaped to hold the in-ear device in an ear, and an audio package (disposed inside casing 203, see infra FIG. 2D) is disposed in the housing, to emit sound. A tympanic membrane measurement unit (TMMU) is structured to measure a movement of a tympanic membrane when the in-ear device 200A is disposed in the ear. In the depicted embodiment, the TMMU includes one or more optical emitters 211 that are positioned in the housing to emit light towards the tympanic membrane, and one or more optical receivers 213 that are positioned in the housing to receive the light reflected from the tympanic membrane. A controller (e.g., an application-specific integrated circuit (ASIC), general purpose processor, or the like), is coupled to the audio package and the TMMU. The controller includes logic that when executed by the controller causes in-ear device 200A to perform operations. Operations may include measuring a movement of the tympanic membrane (e.g., using a deflection of the light from one or more light emitters 211) off of the surface of the tympanic membrane, and in response to measuring the movement of the tympanic membrane, outputting sound from the audio package to destructively interfere with sound received by the tympanic membrane. By measuring the tympanic membrane to inform the "negative" sound output from the audio package, more precise noise cancellation can be achieved.

Many different optical techniques may be used to measure movement of the tympanic membrane. In one embodiment, laser doppler interferometry, which measures deflection of a specific location on the tympanic membrane, may be used. In some embodiments, stroboscopic holography (flashing light and imaging the entire surface of the membrane with an image sensor over time) may be used. However, one of ordinary skill in the art having the benefit of the present disclosure will appreciate that other techniques such as focus-based techniques (e.g., measuring movement via capturing an image going in and out of focus), chromatic (color shifting) techniques, and profilometry techniques may be used.

One of ordinary skill in the art having the benefit of the present discourse will appreciate that the sound output from the audio package may not just be for noise cancellation; the audio package may output music, speech, provide acoustic "transparency" for select sounds, or the like. As shown sound may emanate from a hole in the molding 201 and casing 203.

Figure 2B:
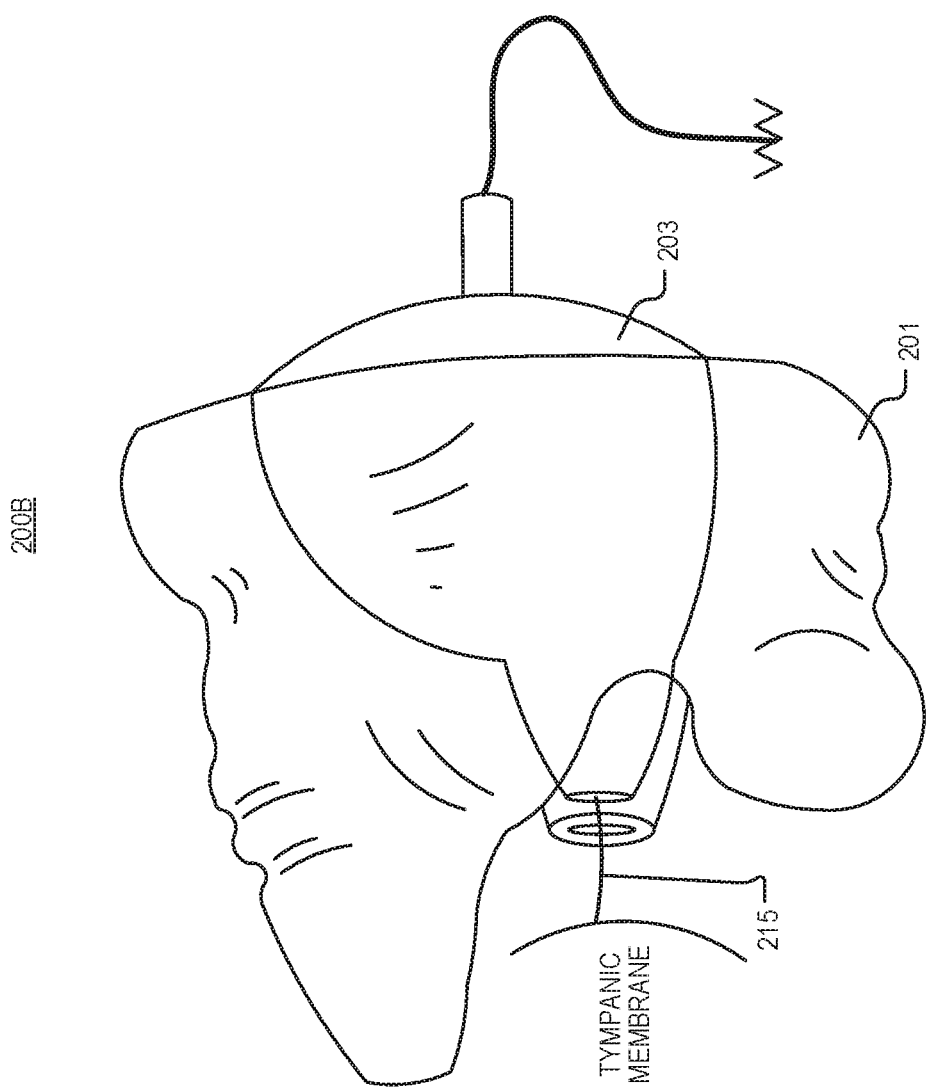
FIG. 2B illustrates an in-ear device, in accordance with an embodiment of the disclosure.

FIG. 2B illustrates an in-ear device 200B, in accordance with an embodiment of the disclosure. In-ear device 200B is similar to device 200A except that the TMMU includes a mechanical deflection measurement system including a fiber 215 extending from the housing to contact the tympanic membrane when the in-ear device is disposed in the ear. The movement of the tympanic membrane is measured using deflection of the fiber 215. Fiber 215 may be an optical fiber (e.g., transparent to some wavelengths of light and exhibiting total internal reflection), and light may be emitted down the fiber by one or more light emitters. As the fiber bends or vibrates with the tympanic membrane, the optical modes of the fiber may change and be measured by optical receivers. The changing optical modes may elicit information about the movement of fiber 215 and the tympanic membrane.

In some embodiments, movement of the fiber may be measured mechanically. For example, the fiber may be vibrated at a rate (e.g., with a piezoelectric actuator) and changes to the vibrational modes may be measured by deformation of (and subsequent voltage changes across) the piezoelectric actuators. In some embodiments, fiber 215 may not be vibrated, and movements received from the tympanic membrane may be measured with an actuator, and a controller may correlate fiber movement to movement of the tympanic membrane.

Figure 2C:
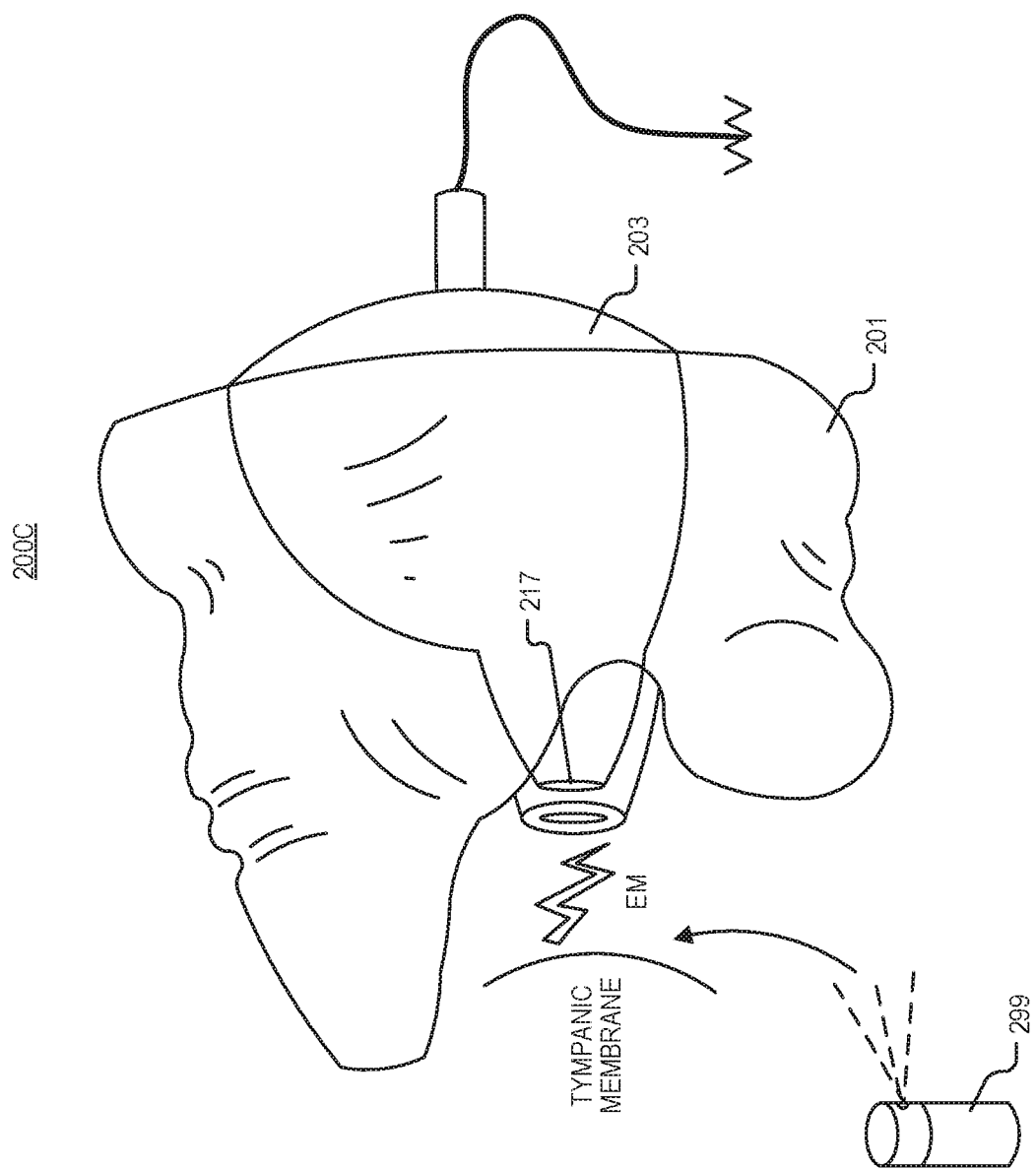
FIG. 2C illustrates an in-ear device, in accordance with an embodiment of the disclosure.

FIG. 2C illustrates an in-ear device, in accordance with an embodiment of the disclosure. In-ear device 200C is similar to device 200A and 200B except that the TMMU includes an electromagnetic detection system 217 (e.g., hall effect sensor, magnetoresistive sensor, or the like) positioned in the housing to measure changes in electromagnetic waves from the tympanic membrane when the in-ear device is disposed in the ear. The movement of the tympanic membrane is measured using the changes in the electromagnetic waves. In some embodiments, the electromagnetic waves emanate from a magnetically active material that is disposed/deposited on the tympanic membrane (e.g., for example the user may apply a spray/drop 299 containing bio-compatible magnetic particles (e.g., iron oxide) to the inside of the ear, or an installed small piece of ferromagnetic material disposed on the tympanic membrane). Thus, when the tympanic membrane vibrates, the movement of the particles is detected by electromagnetic detection system 217.

Figure 2D:
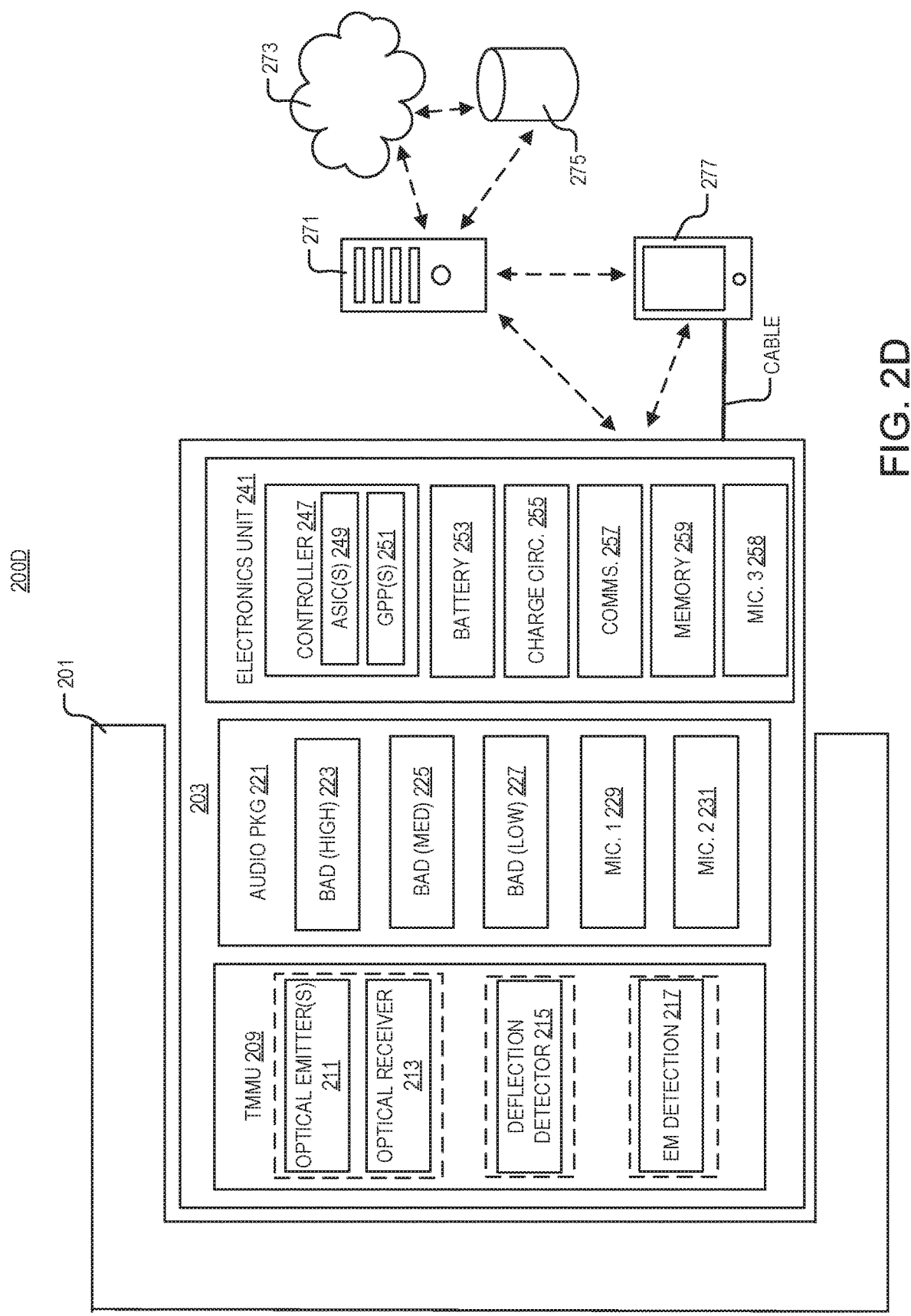
FIG. 2D illustrates a block diagram which is inclusive of the in-ear devices of FIG. 2A-2C, in accordance with an embodiment of the disclosure.

FIG. 2D illustrates a block diagram of the in-ear devices of FIGS. 2A-2C, in accordance with an embodiment of the disclosure. One of ordinary skill in the art will appreciate that this is merely a cartoon illustration, and that the devices depicted are not drawn to scale (and not shown as their actual shape). All of the electronic components may be electrically coupled together to communicate with each other. The devices depicted may have additional or fewer components, in accordance with the teachings of the present disclosure.

Illustrated are four major components: housing (including molding 201 and casing 203), tympanic membrane measurement unit (TMMU) 209, audio package 221, and electronics unit 241.

TMMU may include one or more optical emitters 211, one or more optical receivers 213 (see e.g., FIG. 2A), mechanical deflection measurement system 215 (see e.g., fiber 215 in FIG. 2B), and electromagnetic detection system 217 (see e.g., FIG. 2C). Examples of each of these components have been discussed above in connection with FIGS. 2A-2C. As shown (by dashed lines) these components may or may not be included in all various embodiments of in-ear device 200, however, they are not mutually exclusive. In some embodiments, multiple tympanic membrane measurement techniques may be employed at the same time for signal redundancy or other reasons, in accordance with the teachings of the present disclosure.

As shown, audio package 221 includes audio electronics such as one or more (e.g., three) balanced armature drivers (BADs)—a device that produces sound by vibrating a "reed" using an electromagnetic field—including a high-range BAD 221, a mid-range BAD 225, and a low range BAD 227 to produce high, medium, and low pitches, respectively. However, in other embodiments other sound emitting devices may be used (e.g., cone/coil based speakers, or the like). Audio package 221 also includes one or more microphones (e.g., MIC. 1 229, MIC. 2 231) which may have different sized diaphragms, materials, orientations (e.g., one facing towards the external world, and one facing toward the user's ear canal). Microphones 229 and 231 may be used to record external sounds, and in response to receiving the external sound data with controller 247, the in-ear device may emit sound from audio package to reduce a magnitude (e.g., through destructive interference of the sound waves) of the external sound received by the ear drum in the user's ear.

In one example, noise cancellation may be achieved by collecting external sound (e.g., sound emanating from outside the ear, either from within the user's own body—chewing, coughing, breathing, etc.—or from outside the user's body—car horns, engine noise, etc.) with microphones 229 and 231. In response to collecting the external sound, sound may be output from the audio package 221 to destructively interfere with at least some of the sound reaching the tympanic membrane. Thus, both the movement of the tympanic membrane and sound recorded with microphones 229 and 231 may be used to inform the sound generated by audio package 221 to destructively interfere with unwanted noises/sounds. This may be accomplished by the controller 247 analyzing the external sound, using predictive models included in the logic, to generate a profile of the sound that will destructively interfere with external sound received by the tympanic membrane. The predictive model may use the periodic nature of sound waves that our ears can hear to determine when these waves will hit the tympanic membrane (since the speed of sound in air is known, along with the approximate distance between in-ear device 200D and the tympanic membrane), and output sound from audio package 221 to destructively interfere with the unwanted sound waves.

It is appreciated that the device herein may not only cancel sound, but amplify select sounds, provide on-demand sound transparency (e.g., recognize sounds and let them "pass though" the device as if they were heard naturally), translate language, provide virtual assistant services (e.g., the headphones record a question, send the natural language data to cloud 273 for processing, and receive a natural language answer to the question), or the like. As stated, one or more of microphones 229 and 231 may be canal microphones (e.g., facing into the ear canal to receive sound in the ear canal such as speech or other sounds generated by the user). The canal microphones may be used to receive the user's speech (e.g., when in-ear device 200D is used to make a phone call) and transmit the recorded sound data to an external device. Canal microphones may also be used for noise cancellation and noise transparency functionality to detect noises made by the user (e.g., chewing, breathing, or the like) and cancel these noises in the occluded (by in-ear device 200) ear canal. It is appreciated that user generated noises can seem especially loud in an occluded canal, and accordingly, it may be desirable to use noise cancellation technologies described herein to cancel these sounds in addition to external sounds.

Electronics package 241 includes a controller 247, which may include one or more application-specific integrated circuits (ASICs) 249 to handle specific signal processing tasks, and/or one or more general purpose processors (GPPs) 251. Controller may include logic (e.g., implemented in hardware, software, on the cloud/across a distributed system, or a combination thereof) that when executed by the controller causes the in-ear device to perform a variety of operations. Operations may include playing music/audio, performing noise cancellation computations, or the like. Battery 253 (e.g., a lithium-ion battery or the like) or other energy storage device (e.g., capacitor) is also included in electronics package 241 to provide power to controller 247 and other circuitry. Charging circuitry 255 (e.g., inductive charging loop, direct plug in, or the like) is coupled to battery 253 to charge battery 253. Communications module 257 (e.g., transmitter, receiver, or transceiver) is coupled to communicate with one or more external devices (e.g., wireless router, smart phone, tablet, cellphone network, etc.) via WiFi, Bluetooth, or other communication protocol. In the depicted embodiment, electronics package 241 also includes one or more microphones (e.g., MIC. 3 258). This may serve the same purpose as the microphones in audio package 221: record sounds for uploading to an external device, noise cancellation functionality, or noise transparency functionality. It is appreciated that many of the same electronic devices may be included in both audio package 221 and electronics package 241, and that the electronic devices may be combined in any suitable manner, in accordance with the teachings of the present disclosure.

As shown, communication circuitry 257 may communicate with a smart phone 277 or other portable electronic device, and/or one or more servers 271 and storage 275 which are part of the "cloud" 273. Data may be transmitted to the external devices from in-ear device 200, for example, recordings from microphones 229/231 may be sent to smart phone 277 and uploaded to the cloud. Conversely, data may be downloaded from one or more external devices; for example, music may be retrieved from smart phone 277 or directly from a WiFi network (e.g., in the user's house). The smart phone 277 or other remote devices may be used to interact with, and control, in-ear device 200D manually (e.g., through a user interface like an app) or automatically (e.g., automatic data synch). In some embodiments, the one or more external devices depicted may be used to perform calculations that are processor intensive, and send the results back to the in-ear device 200D.

FIG. 3 illustrates a method of using an in-ear device (e.g., devices depicted in FIGS. 2A-2D), in accordance with an embodiment of the disclosure. One of ordinary skill in the art will appreciate that blocks 301-311 may occur in any order and even in parallel. Additionally, blocks may be added to, or removed from, method 300, in accordance with the teachings of the present disclosure.

Block 301 shows measuring a movement of a tympanic membrane in an ear using a tympanic membrane measurement unit (TMMU) attached to an in-ear device (e.g., head phone type device). As described above, in one embodiment measuring movement may include emitting light (e.g., coherent or collimated light) with one or more optical emitters (e.g., light emitting diodes or lasers) when the in-ear device is disposed in the ear, and receiving the light reflected from the tympanic membrane with one or more optical receivers (e.g., photodiodes arranged in a 1D or 2D array). Substantially collimated light may be emitted from the light emitters, and then deflection of the tympanic membrane (due to incident external sound) may result in the reflected light beam changing its terminal location on the sensor, based on the movement of the light beam on the sensor it is possible to determine a movement of the tympanic membrane.

As described above, in some embodiments, measuring the movement of the tympanic membrane may be achieved by measuring a mechanical deflection using a mechanical deflection measurement system including a fiber (e.g., a transparent polymer or glass fiber with an optical emitter and receiver coupled to one side) extending from the in-ear device to contact the tympanic membrane. As stated above, when the fiber is in contact with the membrane, vibration of the membrane can be measured optically or mechanically through the fiber.

In one embodiment, electromagnetic waves are received by the in-ear device using an electromagnetic detection system to measure changes in electromagnetic waves (e.g., using a Hall Effect sensor or the like coupled to the controller) from the tympanic membrane. This may be achieved by depositing (e.g., with a spray/drops of a suspension, placing a metal chip on the tympanic membrane, or the like) a magnetically active material (e.g., iron, iron oxide, etc.) on the tympanic membrane, and the electromagnetic waves emanate from the magnetically active material. These waves may be measured by sensors in the in-ear device.

Block 303 illustrates calculating, using a controller and the movement measured by the TMMU, a waveform of the sound to destructively interfere with external sound received by the tympanic membrane. The external sound waves reaching the tympanic membrane can be physically observed using the techniques above, thus providing the controller very accurate information about the "anti-sound" that the in-ear device needs to produce to provide noise cancellation. The controller may include circuitry to take the measurements of the TMMU and convert these measurements into information about the sound reaching the eardrum. In some embodiments, measurements of the tympanic membrane (regardless of the measurement technique employed) may be received by an analog to digital converter, pass through an anti-aliasing filter, and an anti-sound profile—that is predistorted to compensate for nonlinearity in the transducer (e.g., speaker or balanced armature driver)—may be generated that will be used to output the anti-sound.

Due to the periodic nature of sound waves, measurements of the tympanic membrane may be used (in conjunction with predictive models) to produce the anti-sound from the audio package. In some embodiments, linear predictive models may be used. In other or the same embodiments, machine learning techniques (such as long short-term memory (LSTM), neural nets, or the like) may be trained on a corpus of audio data to look ahead and see how external sounds will vibrate the tympanic membrane. Moreover, these models may be trained to recognize patterns in the waveforms of external sounds (e.g., the algorithms may be trained to recognize the sonic profile of a footstep and cancel footstep noises).

Block 305 depicts in response to measuring the movement of the tympanic membrane, outputting sound from an audio package (e.g., using speakers or other devices) disposed in the in-ear device to destructively interfere with sound received by the tympanic membrane.

Block 307 shows collecting external sound with a microphone (e.g., any sound wave-to-electrical transducer—condenser microphone, piezoelectric microphone, or the like) disposed in the in-ear device. External sound may be sound generated anywhere outside the ear (including, as described above, sound originating from other locations in the user's body).

Block 309 depicts calculating, using the controller and the external sound entering the ear, the waveform of the sound to destructively interfere with sound received by the tympanic membrane. As discussed above, external sound information may be used in conjunction with, or in isolation from (depending on the operating conditions), the tympanic membrane measurement to inform the controller of the "anti-sound" that need to be output from audio package to cancel out external sounds.

Block 311 illustrates in response to collecting the external sound, outputting sound from the audio package to destructively interfere with sound received by the tympanic membrane. For example, if the external sound follows a sinusoidal wave, the sound output from the audio package may follow a similar sinusoidal wave having a substantially equal and opposite magnitude to destructively interfere with the external sound. However, one of skill in the art will appreciate that the external sound may have a variety of waveforms, and that the device may output complementary waveforms to destructively interfere with the external sound.

As shown elsewhere, the in-ear device may perform other operations such as communicating with external devices using a communications module (e.g., RFID, Bluetooth, WiFi, or the like) disposed within the housing. Additionally, in some wireless embodiments, power may be provided to the TMMU and audio package with a battery disposed in the in-ear device, and the battery may be charged with a charging system (e.g., direct connection port, inductive charging loop, or the like) disposed in the in-ear device. In one embodiment, in ear devices, or parts of in-ear devices, may fit into a small box with slots shaped to receive the in-ear devices, and the devices may charge via inductive or direct power charging.

In the depicted embodiment, the method 400 repeats itself while the noise canceling functionality of the device is enabled. Moreover, as discussed, the processes depicted may be occurring at the same time.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible machine-readable storage medium includes any mechanism that provides (i.e., stores) information in a non-transitory form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. A system, comprising:
   a magnetically active material deposited on a tympanic membrane of an ear, wherein the magnetically active material generates electromagnetic waves; and
   an in-ear device, comprising:
   a housing shaped to hold the in-ear device in the ear;
   an audio package, disposed in the housing, to emit sound;
   a tympanic membrane measurement unit (TMMU) structured to measure a movement of the tympanic membrane caused by external sound received by the tympanic membrane, wherein the TMMU includes:
   an electromagnetic detection system positioned in the housing to measure changes in the electromagnetic waves from the magnetically active material when the in-ear device is disposed in the ear, wherein the movement of the tympanic membrane is measured using the changes in the electromagnetic waves; and a controller coupled to the audio package and the TMMU, wherein the controller includes logic that when executed by the controller causes the in-ear device to perform operations, including:
    receiving the movement of the tympanic membrane measured by the TMMU;
    determining a waveform of cancellation sound based at least on the movement of the tympanic membrane; and
    outputting the cancellation sound from the audio package to destructively interfere with the external sound received by the tympanic membrane.

2. The system of claim 1, wherein the TMMU and the controller are disposed in the housing.

3. The system of claim 1, further comprising a microphone coupled to the controller and mounted in or on the housing, wherein the controller further includes logic that when executed by the controller causes the in-ear device to perform operations, including:
    collecting external sound with the microphone;
    wherein determining the waveform of the cancellation sound based at least on the movement of the tympanic membrane includes determining the waveform of the cancellation sound based at least on the movement of the tympanic membrane and the external sound collected with the microphone.

4. The system of claim 3, wherein determining the waveform of the cancellation sound based at least on the movement of the tympanic membrane and the external sound collected with the microphone includes:
    analyzing the external sound collected with the microphone using predictive models.

5. The system of claim 1, wherein the TMMU includes:
    one or more optical emitters disposed in or on the housing and oriented to emit light towards the tympanic membrane when the in-ear device is disposed in the ear; and
    one or more optical receivers disposed in or on the housing and oriented to receive the light reflected from the tympanic membrane, wherein the movement of the tympanic membrane is measured using the light reflected from the tympanic membrane.

6. The system of claim 5, wherein the one or more optical receivers include an image sensor to output an image of the tympanic membrane, and wherein the movement of the tympanic membrane is measured using the image.

7. The system of claim 1, wherein the TMMU includes:
    a mechanical deflection measurement system including a fiber extending from the housing to contact the tympanic membrane when the in-ear device is disposed in the ear, and wherein the movement of the tympanic membrane is measured using deflection of the fiber.

8. The system of claim 1, further comprising:
    a battery disposed within the housing and coupled to supply power to the TMMU, the controller, and the audio package; and
    charging circuitry disposed in the housing and coupled to charge the battery.

9. A method of noise cancellation, comprising:
    measuring a movement of a tympanic membrane in an ear using a tympanic membrane measurement unit (TMMU) attached to an in-ear device, wherein the movement of the tympanic membrane is caused by external sound reaching the tympanic membrane;
    analyzing at least the movement of the tympanic membrane measured by the TMMU using a predictive model trained by a machine learning technique to generate a waveform of cancellation sound that will destructively interfere with the external sound when received by the tympanic membrane; and
    outputting the cancellation sound from an audio package disposed in the in-ear device to destructively interfere with external sound received by the tympanic membrane.

10. The method of claim 9, further comprising:
collecting external sound with a microphone disposed in the in-ear device;
wherein analyzing at least the movement of the tympanic membrane measured by the TMMU using the predictive model trained by the machine learning technique to generate the waveform of cancellation sound that will destructively interfere with the external sound when received by the tympanic membrane includes:
    analyzing at least the movement of the tympanic membrane and the external sound collected with the microphone using the predictive model.

11. The method of claim 9, wherein measuring the movement of the tympanic membrane includes:
    emitting light with one or more optical emitters when the in-ear device is disposed in the ear; and
    receiving the light reflected from the tympanic membrane with one or more optical receivers.

12. The method of claim 11, wherein receiving the light includes receiving the light with an image sensor and using an image output from the image sensor to measure the movement.

13. The method of claim 9, wherein measuring the movement of the tympanic membrane includes:
    measuring a mechanical deflection using a mechanical deflection measurement system including a fiber extending from the in-ear device to contact the tympanic membrane when the in-ear device is disposed in the ear.

14. The method of claim 9, wherein measuring the movement of a tympanic membrane includes:
    receiving electromagnetic waves using an electromagnetic detection system positioned in the in-ear device to measure changes in electromagnetic waves from the tympanic membrane when the in-ear device is disposed in the ear, wherein the electromagnetic waves are generated from a magnetically active material deposited on the tympanic membrane.

15. The method of claim 9, further comprising communicating with an external device using a communications module disposed within the housing.

16. The method of claim 9, further comprising:
providing power to the TMMU and audio package with a battery disposed in the in-ear device; and
charging the battery with a charging system disposed in the in-ear device.

17. An in-ear device, comprising:
a housing shaped to hold the in-ear device in an ear;
an audio package, disposed in the housing, to emit sound;
a tympanic membrane measurement unit (TMMU) structured to measure a movement of a tympanic membrane in the ear caused by external sound received by the tympanic membrane, wherein the TMMU includes a mechanical deflection measurement system including a fiber extending from the housing to contact an external surface of the tympanic membrane when the in-ear device is disposed in the ear, and wherein the movement of the tympanic membrane is measured using deflection of the fiber;
a controller coupled to the audio package and the TMMU, wherein the controller includes logic that when executed by the controller causes the in-ear device to perform operations, including:

receiving the movement of the tympanic membrane measured by the TMMU; and in response to the movement of the tympanic membrane, outputting sound from the audio package to destructively interfere with the external sound received by the tympanic membrane.

18. The device of claim 17, wherein the fiber is an optical fiber, and wherein measuring the movement of the tympanic membrane using deflection of the fiber includes measuring an optical mode of the fiber as the fiber bends or vibrates with the tympanic membrane.

19. The device of claim 17, wherein the TMMU and the controller are disposed in the housing.

20. The device of claim 17, further comprising:

a battery disposed within the housing and coupled to supply power to the TMMU, the controller, and the audio package; and charging circuitry disposed in the housing and coupled to charge the battery.

\* \* \* \* \*